US005691189A

United States Patent [19]
Kurtz et al.

[11] Patent Number: 5,691,189
[45] Date of Patent: Nov. 25, 1997

[54] SACCHAROMYCES CEREVISIAE EXPRESSING $M_2$ PROTEIN OF INFLUENZA A VIRUS

[75] Inventors: Stephen E. Kurtz, Princeton; Mark Krystal, Cranbury, both of N.J.

[73] Assignee: Bristol-Myers Squibb Company, Princeton, N.J.

[21] Appl. No.: 556,124

[22] Filed: Nov. 9, 1995

Related U.S. Application Data

[63] Continuation of Ser. No. 183,545, Jan. 19, 1994, abandoned.

[51] Int. Cl.$^6$ ............................. C12N 1/15; C12N 1/19
[52] U.S. Cl. ................... 435/254.21; 435/320.1
[58] Field of Search ........................... 435/69.1, 91.2, 435/172.3, 254.21, 320.1; 536/23.72

[56] References Cited

PUBLICATIONS

J. A. Anderson et al., Proc. Natl. Acad. Sci. U.S.A., 89, pp. 3736–3740, 1992.
H. Sentenac et al., Science, 256, pp. 663–666.
L. J. Holsinger et al., Virology, 183, pp. 32–43, 1991.
R. J. Sugrue et al., Virology, 180, pp. 617–624, 1991.
L. H. Pinto et al., Cell, 69, pp. 517–528, 1992.
A. J. Hay, Seminars in Virology, 3, pp. 21–30, 1992.
S. Markushins et al., Virus Research, 10, pp. 263–272, 1988.
R. A. Black et al., J. Gen. Virol., 74, pp. 143–146, 1993.
H. Bussey et al., Experientia, 46, pp. 193–200, 1990.
B. Martinac et al., PNAS, 87, pp. 6228–6232, 1990.
Kagan, Nature, 302, pp. 709–711, 1983.
S. L. Zebedee et al., Journal of Virology, vol. 62, No. 8, pp. 2762–2772, 1988.
R. A. Lamb et al., Cell, vol. 40, pp. 627–633, 1985.
S. L. Zebedee et al., Journal of Virology, vol. 56, No. 2, pp. 502–511, 1985.
M. S. P. Samsom et al., Protein Engineering, vol. 6, No. 1, pp. 65–74, 1993.
C. Wang et al., Journal of Virology, vol. 67, No. 9, pp. 5585–5594, 1993.
K. C. Duff et al., Virology, 190, pp. 485–489, 1992.
P. G. Hughey et al., Journal of Virology, vol. 66, No. 9, pp. 5542–5552, 1992.
A. J. Hay, Seminars in Virology, vol. 3, pp. 21–30, 1992.
K. C. Duff et al., Biochimica et Biophysica Acta, 1145, pp. 149–156, 1993.
D. A. Steinhauer et al., Proc. Natl. Acad. Sci. USA, vol. 88, pp. 11525–11529, 1991.
S. Grambas et al., Virology, vol. 190, pp. 11–18, 1992.
R. B. Belshe et al., Journal of Virology, vol. 62, No. 5, pp. 1509–1512, 1988.
F. Ciampor et al., Virus Research, vol. 22, pp. 247–258, 1992.
J. J. Skehel, Nature, vol. 358, pp. 110–111, 1992.
S. L. Zebedee et al., Proc. Natl. Acad. Sci. USA, vol. 86, pp. 1061–1065, 1989.
C. Scholtissek et al., J. Gen. Virology, vol. 44, pp. 807–815, 1979.
A. Helenius, Cell, vol. 69, pp. 577–578, 1992.
S. Grambas et al., Virology, vol. 191, pp. 541–549, 1992.
R. A. Black et al., Journal of General Virology, vol. 74, pp. 143–146, 1993.
K. C. Duff et al., Federation of European Biochemical Societies, vol. 311, No. 3, pp. 256–258, 1992.

*Primary Examiner*—James Ketter
*Attorney, Agent, or Firm*—Timothy J. Gaul

[57] ABSTRACT

A modified *Saccharomyces cerevisiae* cell, wherein the cell expresses the Influenza virus ion channel protein $M_2$. Also disclosed is a process for detecting modulators of $M_2$, which comprises (a) treating such modified *Saccharomyces cerevisiae* cells with a test substance, and (b) assessing growth in the presence of a test substance, wherein a change in growth signals that the test substance is an $M_2$ modulator. $M_2$ inhibitors are useful anti-viral agents.

10 Claims, 5 Drawing Sheets

ATG AGT CTT CTA ACC GAG GTT GAA ACG CCA ATC AGA AAC GAA TGG GGG
Met Ser Leu Leu Thr Glu Val Glu Thr Pro Ile Arg Asn Glu Trp Gly
1                                     10

TGC AGA TGC AAC GAT TCA AGT GAT CCT CTC GTC ATT GCA GCA AAT ATC
Cys Arg Cys Asn Asp Ser Ser Asp Pro Leu Val Ile Ala Ala Asn Ile
         20                                         30
                                                       Ser

ATT GGA ATC TTG CAC TTG ATA TTG TGG ATT CTT GAT CGT CTT TTT TTC
Ile Gly Ile Leu His Leu Ile Leu Trp Ile Leu Asp Arg Leu Phe Phe
                       40

AAA TGC ATT TAT CGT CGC T TT AAA TAC GGT TTG AAA AGA GGG CCT TCT
Lys Cys Ile Tyr Arg Arg Phe Lys Tyr Gly Leu Lys Arg Gly Pro Ser
     50                                           60

ACG GAA GGA GTG CCA GAG TCT ATG AGG GAA GAA TAT CGA AAG GAA CAG
Thr Glu Gly Val Pro Glu Ser Met Arg Glu Glu Tyr Arg Lys Glu Gln
                    70                                       80

CAG AAT GCT GTG GAT GTT GAC GAT GGT CAT TTT GTC AAC ATA GAG CTG
Gln Asn Ala Val Asp Val Asp Asp Gly His Phe Val Asn Ile Glu Leu
                                    90

GAG TAA
Glu

FIG. 2

SACCHAROMYCES CEREVISIAE EXPRESSING M₂ PROTEIN OF INFLUENZA A VIRUS

This is a continuation of application Ser. No. 08/183,545 filed on Jan. 19, 1994, now abandoned.

FIELD OF THE INVENTION

This invention relates to yeast, recombinant DNA techniques, and to processes for detecting inhibitors and/or activators of viral ion channels.

BACKGROUND OF THE INVENTION

Ion uptake in yeast is accomplished through the concerted actions of transporter proteins with ion selectivity and the electrochemical gradient established by the plasma membrane hydrogen ion ATPase. For example, potassium ions are taken up by transporter proteins encoded by two genes, TRK1 and TRK2, and exchanged stoichiometrically for each hydrogen ion extruded from the cell by the ATPase. Rodriguez-Navarro and Ramos, *J. Bacteriol*, 159: 940–945 (1984); Gaber, Styles, and Fink, *Mol. Cell Biol.* 8: 2848–2859 (1988); Ko and Gaber, *Genetics* 125: 305–312 (1990). Serrano, R.(1991 ) In *The Molecular Biology of the Yeast Saccharomyces*, Broach, J. R. et al., eds. Cold Spring Harbor, pp 523–585. Perturbations of the electrochemical gradient permit essential ions such as potassium to leak from the cell, resulting in cell death.

Several laboratories have used yeast strains defective in potassium ion uptake as hosts for expressing ion channels from other organisms. Certain ion channels from *Arabidopsis thaliana* restore potassium ion uptake function and permit growth of the strain on media with low levels of potassium ions. Anderson, et al., *Proc. Natl. Acad. Sci. U.S.A.* 89: 3736–3740 (1992); Sentenac, et al. (1992), *Science* 256: 663–666.

The M₂ protein of Influenza A virus is a 97 amino acid polypeptide containing a single membrane-spanning region. In the virus and infected cell membranes, M₂ polypeptides associate into tetramers to form ion channels, thereby providing a function essential for virus replication. Holsinger, L. J. and Lamb, R. A. (1991), *Virology* 183: 32–43; Sugrue R. L. and Hay, A. J. (1991), *Virology* 180: 617–624; Pinto, L., et al. (1992), *Cell* 69: 517–528. The available therapeutic agents for Influenza A virus, amantadine and rimantadine, function by blocking M₂ ion channel activity. Hay, A.(1992), *Seminars in Virology* 3: 21–30. Inhibition studies with amantadine suggest that M₂ functions at both early and late stages in virus infection by permitting ion flow across various membranes. New inhibitors of the M₂ channel would be effective antiviral agents. A need exists, therefore, for methods of screening for inhibitors and/or activators of the M₂ channel.

BRIEF DESCRIPTION OF THE INVENTION

The present invention concerns a modified *Saccharomyces cerevisiae* cell, wherein the cell expresses a nucleic acid sequence for an M₂ protein or a functional derivative or mutant thereof. The yeast cell expresses this protein through its normal transcription and translation mechanisms.

The present invention further concerns a process for detecting modulators of the M₂ channel, which comprises:

(a) treating *Saccharomyces cerevisiae* cells with a test substance, wherein the *Saccharomyces cerevisiae* cells express the M₂ protein or a functional derivative or mutant thereof; and (b) assessing growth in the presence of a test compound; wherein a change in growth in the presence of the test compound signals that the test compound is a modulator of the M₂ channel. This process is thus useful for detecting inhibitors of M₂ channel function, which are useful as anti-influenza agents.

Functional expression of ion channels in yeast provides a general means for detecting channel modulators. Compounds that modulate channel function am detected by observing alterations in growth, which is dependent on channel function: Expression of ion channels in yeast is not restricted to restoration of uptake functions and, depending on the particular channel, may result in a range of effects on the host.

The present inventors have designed a method to detect inhibitors of the M₂ protein of Influenza A. The aforementioned principle of this screen, growth rescue, is based on the observation by the inventors that expression of high levels of M₂ protein in *Saccharomyces cerevisiae* impairs growth. The inventors validated this observation by rescuing the growth impairment with amantadine, a known blocker of M₂ function. The inventors obtained genetic evidence to support this observation by converting an amantadine-resistant M₂ allele to amantadine-sensitivity. They subsequently observed amantadine-dependent growth rescue in a strain having the amantadine-sensitive M₂ allele.

BRIEF DESCRIPTION OF THE FIGURES

FIG. 1 shows a Western blot of M₂ protein using rabbit polyclonal antisera against the M₂ protein. Strains contained either the pGAL vector (designated V), a single-copy plasmid expressing M₂ (designated M₂single) or a multi-copy plasmid expressing M₂ (designated M₂multi). Extracts prepared from influenza virus-infected and mock-infected Martin Darby canine kidney cells (designated MDCK) are included as controls. These data indicate that yeast cells containing the multi-copy plasmid produce high levels of M₂ protein when grown on inducing media (galactose).

FIG. 2 shows a modified genomic sequence for the M₂ gene (SEQ. ID. NO.: 1) and the resulting amino acid sequence (SEQ. ID. NO.: 2). The sequence was obtained from a cDNA clone constructed at Bristol-Myers Squibb and contains three differences from the sequence published in Markushins et al. (1988), *Virus Research* 10: 263–272. Amino acid residues 26 to 43, which define the proposed transmembrane region of the protein, are underlined in FIG. 2. The asparagine (Asn) to serine (Ser) change at amino acid 31, which converts the protein to amantadine-sensitivity, is indicated.

DETAILED DESCRIPTION OF THE INVENTION

Figure 1:
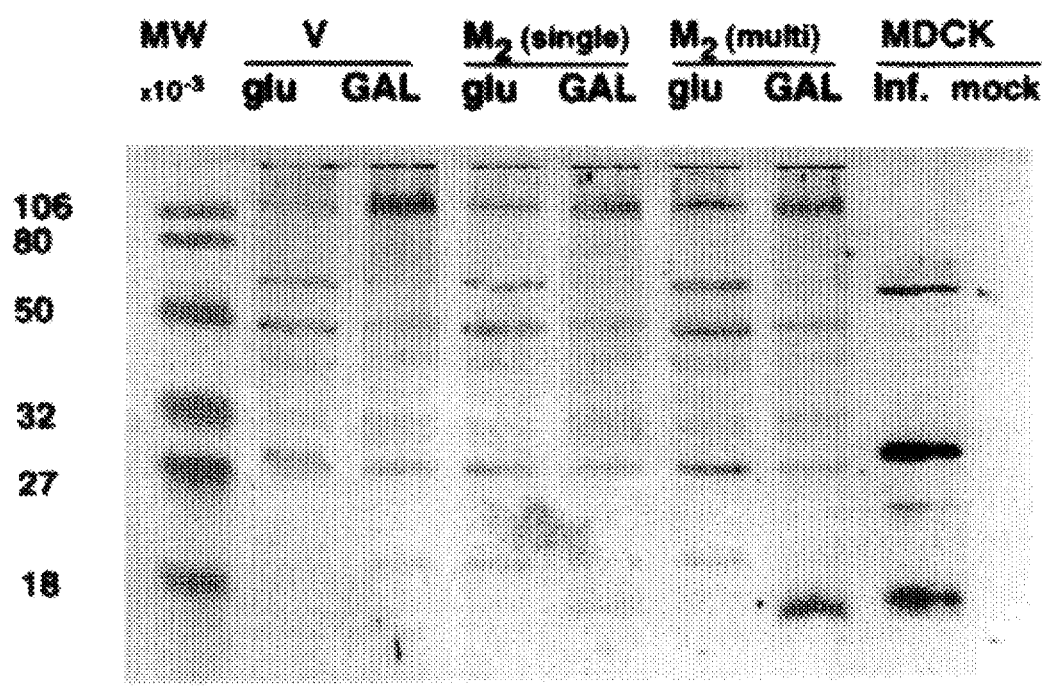
FIG. 1 is a Western blot indicating the levels of M₂ protein produced in yeast. Protein extracts were prepared by lysing log phase cells in a vortex with glass beads. The concentration of total protein was determined using the Bradford reagent. Equivalent amounts of extract (100 µg) from each strain were separated by electrophoresis on 12.5% sodium dodecyl sulfate-polyacrylamide gels (SDS-PAGE). After electrophoresis, gels were transferred to nitrocellulose for Coomassie Blue staining or reaction with anti-M₂ antisera (gift of Paul Rota, CDC).

The following definitions apply to the terms as used throughout this specification, unless otherwise limited in specific instances.

The term "modified" as used with respect to a cell refers to a cell in which the wild-type genome has been altered by addition of one or more heterologous genes, a deficiency in one or more wild-type genes, or a combination thereof. Such modifications may be carried out by transformation and homologous recombination through techniques well understood by those having ordinary skill in the art.

The term "an $M_2$ protein" refers to a protein having at least the smallest portion of the full-length wild-type $M_2$ protein that can result in growth impairment in *Saccharomyces cerevisiae*. Proteins having residues 26 to 43 of FIG. 2 are preferred for the $M_2$ protein.

The term "a functional derivative or mutant thereof" as used with respect to a protein refers to a protein differing from the subject protein by one or more amino acid residues but still having the biochemical function of the protein and greater than about 90% sequence homology. In the case of the $M_2$ protein, a "functional derivative or mutant thereof" refers to such proteins that have ion transport activity but do not have the identical amino acid sequence shown in FIG. 2. Such derivatives and mutants may include proteins that differ from the wild-type protein by amino acid substitutions, deletions, disruptions, and the like. Such differences may be accomplished by genetic means, using such techniques as site-directed mutagenesis or mutagenic polymerase chain reaction (PCR) prior to translation, or by chemical means, using proteases and/or ligases after translation. Functional ion transport activity may be determined by the growth and growth rescue assays described herein (i.e., as in FIGS. 3 and 4).

The present invention may employ the amantadine-sensitive strain SGY1444, which contains pGAL::$M_2$ (N31S) construction in pYES2, ATCC No. 74266. The ATCC designation reflects a deposit under the Budapest Treaty with the Amedcan Type Culture Collection, 12301 Parklawn Drive, Rockville, Md. 20852-1776.

These strains contain plasmids that require constant selection on minimal media lacking uracil to ensure their maintenance. The preferred strain background is MATα, ade2-1, can1-100, his3-11.15, leu2-3, 112, trp1-1, ura3-1.

The yeast cell of the present invention begins with a wild type yeast strain with regard to ion channel activity. A variety of viral ion channels may be introduced into this strain to assess whether these channels impair growth. This analysis may reveal ion channels that have been cloned but not yet described physiologically. Each application results in a strain expressing a foreign ion channel, useful in a screen for modulators of the channel.

A yeast strain expressing an ion channel can be adapted to natural products screening. A simple screen design involving growth inhibition or ion uptake in agar plates or in liquid culture may detect compounds that modulate channel function. For screening of activators of an ion channel, the screen may include such modifications such as pH adjustment.

Figure 3:
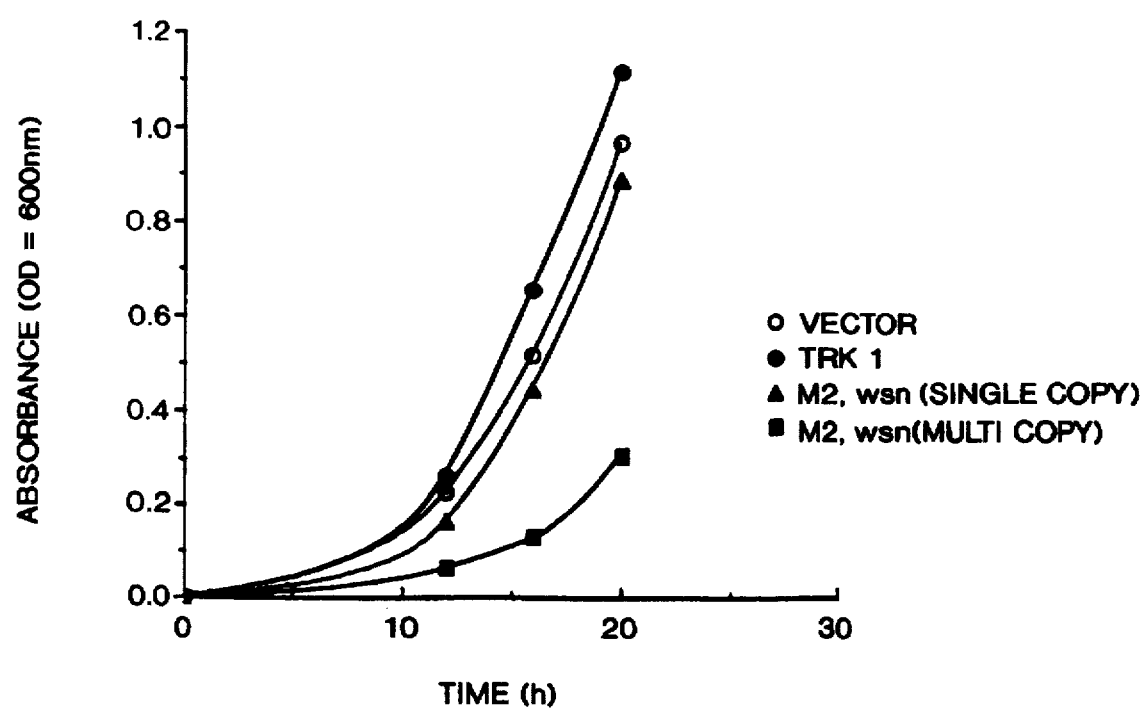
FIG. 3 shows the growth of cells expressing M₂. Cultures of strains containing the vector, single-copy M₂ plasmid or multi-copy M₂ plasmid were grown in inducing media at 30° C. with vigorous aeration. A strain expressing the yeast high affinity potassium ion transporter, TRK1, was included as an additional control. Samples were removed at various intervals and the optical density at 600 nm was determined. Absorbance (A₆₀₀) is plotted versus time (hours).

In the course of developing this system, the inventors introduced plasmids that contain the $M_2$ gene under the transcriptional control of an inducible promoter (GAL 1) into a yeast strain defective in potassium uptake. To analyze $M_2$ expression in the transporter mutant, the inventors compared three different transformed strains: (1) a transformant containing the parent vector lacking an insert, (2) a transformant containing the $M_2$ (WSN) gene expressed on a single-copy plasmid, and (3) a transformant containing the $M_2$ (WSN) gene expressed on a multi-copy plasmid (note that the WSN allele of $M_2$ is amantadine resistant). When these strains were grown on inducing media, expression of $M_2$ protein to levels comparable to those in virus-infected canine kidney cells (MDCK) was detected only in the strain containing the multi-copy plasmids (FIG. 1). Growth of this strain was significantly impaired relative to control strains (FIG. 3). Thus, levels of $M_2$ expression and growth impairment correlate directly. This observation is consistent with studies of $M_2$ expression in baculovirus-infected insect cells and in Xenopus oocytes. Black, R. et al., (1993), *J. Gen Virol.* 74: 143–146. This result allowed use of wild type yeast incorporating the $M_2$ gene rather than only strains defective in potassium uptake.

Figure 4:
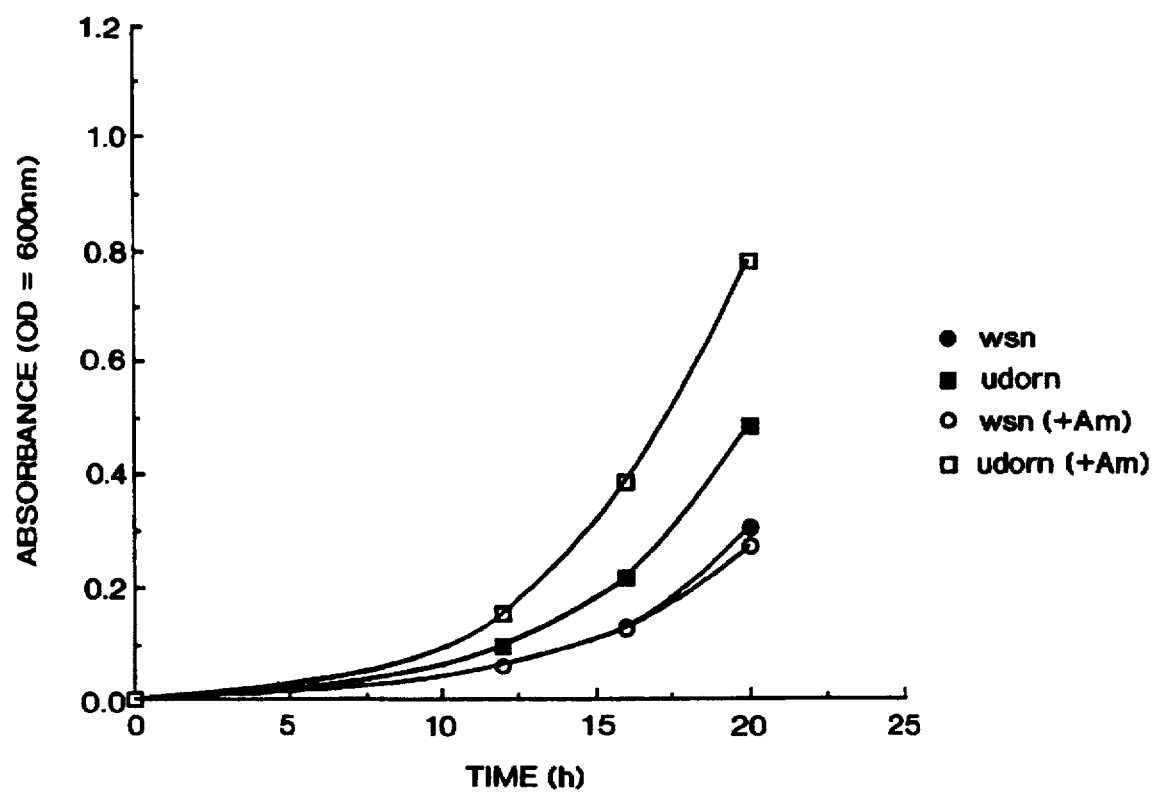
FIG. 4 illustrates growth rescue by addition of amantadine to a culture of cells expressing the Udorn $M_2$ (gift of Robert Lamb, Northwestern University). Cultures of strains containing the amantadine-resistant $M_2$ plasmid (WSN) or the amantadine-sensitive $M_2$ plasmid (Udorn) were grown in inducing media at 30° C. with vigorous aeration. Samples were removed at various intervals and the optical density at 600 nm was determined. Absorbance ($A_{600}$) is plotted versus time (hours). Amantadine concentration was 100 µM.
Figure 5:
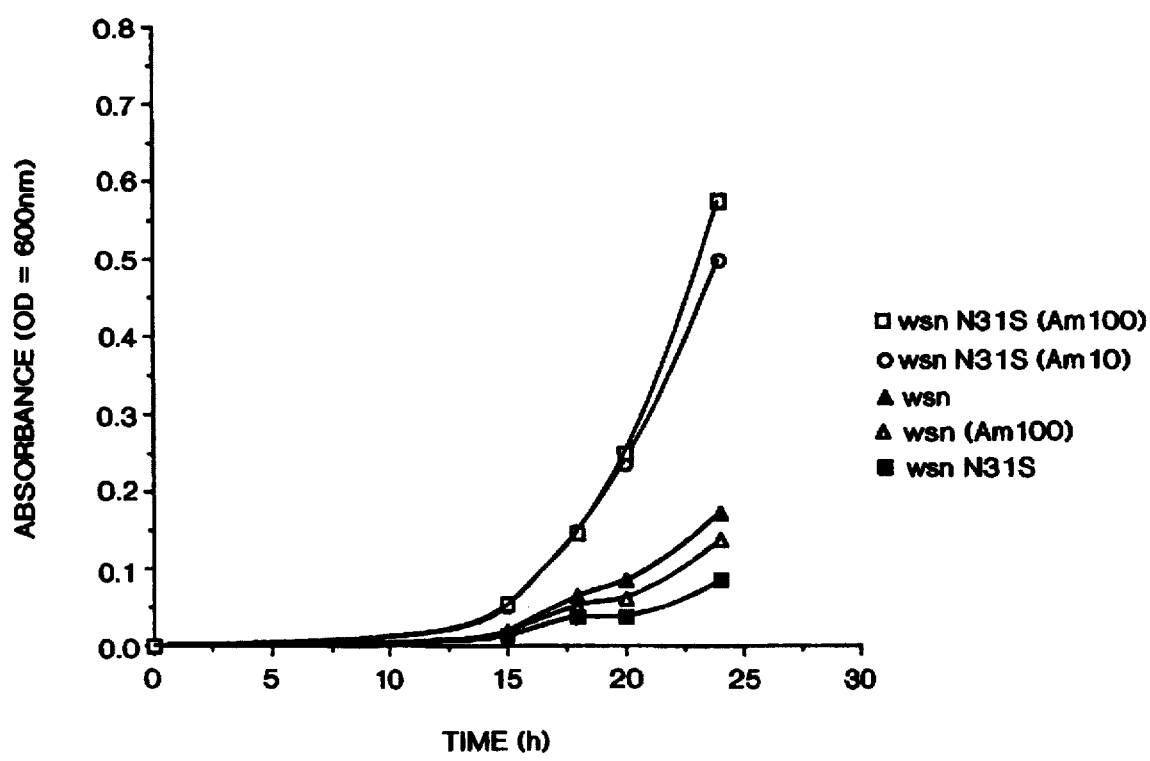
FIG. 5 shows the growth of strains expressing an allele of $M_2$ converted from amantadine-resistance (WSN) to amantadine sensitivity. Cultures of strains containing amantadine-resistant $M_2$ plasmid (WSN) or amantadine-sensitive $M_2$ plasmid (WSN, N31S) were grown in inducing media at 30° C. with vigorous aeration. Samples were removed at various intervals and the optical density at 600 nm was determined. Absorbance ($A_{600}$) is plotted versus time (hours). Amantadine was included at concentrations of 10 and 100 µM.

To confirm this interpretation, the inventors examined growth of yeast transformants expressing the Udorn allele of $M_2$, which is amantadine-sensitive. In the presence of amantadine, these transformants grow at near wild-type rates, whereas growth of the transformants expressing the amantadine-resistant WSN allele is not remediated with amantadine (FIG. 4). Additional genetic evidence was obtained from an experiment in which the amantadine-resistant allele of $M_2$ (WSN) was converted back to amantadine-sensitivity by changing amino acid 31 from asparagine to serine (WSN, N31S). Both WSN alleles are toxic when overexpressed in yeast; however, only the toxicity of the WSN(N31S) allele is blocked by addition of amantadine to the media (FIG. 5).

While not intending to be constrained by theory, the present inventors suggest that $M_2$ exerts its effect on yeast cells by functioning as an unregulated pore in a manner similar to killer toxin, which disrupts membrane integrity and causes ion leakage. Killer toxin, a low molecular weight polypeptide product of the yeast viral double-stranded RNA (dsRNA), is secreted by most yeast strains. It kills sensitive cells by binding initially to a 1,6-β-D-glucan cell wall receptor (reviewed in Bussey, H. et al., (1990), *Experientia* 46: 193–200). Exposure to toxin results in a rapid inhibition of net proton pumping, which reduces the proton gradient across the plasma membrane. Concomitantly, toxin-treated cells show an inhibition of potassium ion and amino acid uptake, accompanied by acidification of the cytoplasm and potassium ion efflux. Killer toxin has since been shown to form ion channels in liposomes and in bilayers. Martinac, B. et al., (1990), PNAS 87: 6228–6232; Kagan, B., (1983), *Nature* 302: 709–711. The toxicity of $M_2$ in yeast may be the consequence of a similar membrane effect.

DETAILED DESCRIPTION OF THE PREFERRED EMBODIMENT

Construction of Expression Plasmids pGAL::M$_2$. The following oligonucleotides were used to amplify sequences encoding the WSN M$_2$ protein from a full length cDNA clone of segment 7 of WSN virus:

SEQ. ID. NO.: 3
  5'-GGATCCGGAT CCAGCAAAAG
  CAGGTAGATA TTGAAAGATG
  AGTCTTCTAA CCGAGGT    -3' and SEQ. ID. NO.: 4
  5'-TCTAGATCTA GATTACTCCA
  GCTCTATGCT GACAAATG    -3'.

The PCR-amplified product was digested with BamHI and XbaI, gel-purified and cidned into an identically digested pYES2 vector (Invitrogen). The plasmid was verified by standard restriction digests and the insert was analyzed by DNA sequencing.

pGAL::TRK1. The following oligonucleotides were used to amplify sequences encoding the yeast Trk1 protein from a plasmid containing the TRK1 gene (this plasmid was isolated from a yeast genomic library by hybridization with 5' and 3' DNA fragments unique to the TRK1 gene):

SEQ. ID. NO.:5
  5'-CGGGATCCAA AAAATGCATT
  TTAGAAGAAC GATGAG    -3' and

SEQ. ID. NO.:6
  5'-CCCGCTCGAG CGATGAGTGG
  GGATTTTGTC -3'.

The PCR-amplified product was digested with BamHI and XhoI, gel-purified and cloned into identically digested pYEUra3 vector (Clontech). The plasmid was verified by restriction digests and complements a trk1 deletion mutation when expressed in vivo.

Assay for growth

Cultures of strains containing either pYES2 vector, pGAL::TRK1 or pGAL::M$_2$, were grown in inducing media (2% galactose) at 30° C. with vigorous aeration. Optical density was determined at various intervals by measuring absorbance at 600 nm. Amantadine was prepared fresh and added to cultures at the time of induction at 10 and 100 μM final concentrations.

---

What is claimed is:

1. A *Saccharomyces cerevisiae* cell comprising multiple copies of a plasmid that expresses a nucleic acid sequence for a $M_2$ protein or a functional mutant or derivative thereof, wherein the $M_2$ protein or functional mutant or derivative thereof is expressed at a level such that growth of a culture of the cells is impaired.

2. The cell of claim 1, wherein the $M_2$ protein comprises residues 26 to 43 of FIG. 2.

3. The cell of claim 1, wherein the $M_2$ protein has the amino acid sequence of SEQ. ID. NO.: 2.

4. The cell of claim 1, wherein the $M_2$ protein has the amino acid sequence encoded by a nucleic acid having the nucleotide sequence of SEQ. ID. NO.: 1.

5. The cell of claim 1, ATCC 74266.

6. The cell of claim 1, comprising an expression vector for the $M_2$ protein.

7. The cell of claim 1, comprising an expression vector for residues 26 to 43 of FIG. 2.

8. The cell of claim 1, comprising an expression vector for a polypeptide comprising the amino acid sequence of SEQ. ID. NO.: 2.

9. The cell of claim 1, comprising an expression vector having the nucleotide sequence of SEQ. ID. NO.: 1.

10. The cell of claim 6, wherein the expression vector is pGAL.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 294 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..291

( x i ) SEQUENCE DESCRIPTION: SEQ ID NO:1:

```
ATG  AGT  CTT  CTA  ACC  GAG  GTT  GAA  ACG  CCA  ATC  AGA  AAC  GAA  TGG  GGG      48
Met  Ser  Leu  Leu  Thr  Glu  Val  Glu  Thr  Pro  Ile  Arg  Asn  Glu  Trp  Gly
 1              5                        10                       15

TGC  AGA  TGC  AAC  GAT  TCA  AGT  GAT  CCT  CTC  GTC  ATT  GCA  GCA  AAT  ATC      96
Cys  Arg  Cys  Asn  Asp  Ser  Ser  Asp  Pro  Leu  Val  Ile  Ala  Ala  Asn  Ile
               20                        25                       30

ATT  GGA  ATC  TTG  CAC  TTG  ATA  TTG  TGG  ATT  CTT  GAT  CGT  CTT  TTT  TTC     144
Ile  Gly  Ile  Leu  His  Leu  Ile  Leu  Trp  Ile  Leu  Asp  Arg  Leu  Phe  Phe
          35                        40                       45

AAA  TGC  ATT  TAT  CGT  CGC  TTT  AAA  TAC  GGT  TTG  AAA  AGA  GGG  CCT  TCT     192
Lys  Cys  Ile  Tyr  Arg  Arg  Phe  Lys  Tyr  Gly  Leu  Lys  Arg  Gly  Pro  Ser
     50                        55                       60

ACG  GAA  GGA  GTG  CCA  GAG  TCT  ATG  AGG  GAA  GAA  TAT  CGA  AAG  GAA  CAG     240
Thr  Glu  Gly  Val  Pro  Glu  Ser  Met  Arg  Glu  Glu  Tyr  Arg  Lys  Glu  Gln
 65                       70                       75                       80

CAG  AAT  GCT  GTG  GAT  GTT  GAC  GAT  GGT  CAT  TTT  GTC  AAC  ATA  GAG  CTG     288
Gln  Asn  Ala  Val  Asp  Val  Asp  Asp  Gly  His  Phe  Val  Asn  Ile  Glu  Leu
                    85                       90                       95

GAG  TAA                                                                            294
```

Glu (2) INFORMATION FOR SEQ ID NO:2:

(i) SEQUENCE CHARACTERISTICS:
    (A) LENGTH: 97 amino acids
    (B) TYPE: amino acid
    (D) TOPOLOGY: linear (ii) MOLECULE TYPE: protein (xi) SEQUENCE DESCRIPTION: SEQ ID NO:2:

```
Met Ser Leu Leu Thr Glu Val Glu Thr Pro Ile Arg Asn Glu Trp Gly
 1               5                  10                  15
Cys Arg Cys Asn Asp Ser Ser Asp Pro Leu Val Ile Ala Ala Asn Ile
             20                  25                  30
Ile Gly Ile Leu His Leu Ile Leu Trp Ile Leu Asp Arg Leu Phe Phe
         35                  40                  45
Lys Cys Ile Tyr Arg Arg Phe Lys Tyr Gly Leu Lys Arg Gly Pro Ser
     50                  55                  60
Thr Glu Gly Val Pro Glu Ser Met Arg Glu Glu Tyr Arg Lys Glu Gln
 65                  70                  75                  80
Gln Asn Ala Val Asp Val Asp Asp Gly His Phe Val Asn Ile Glu Leu
                 85                  90                  95
Glu
```

(2) INFORMATION FOR SEQ ID NO:3:

(i) SEQUENCE CHARACTERISTICS:
    (A) LENGTH: 57 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:3:

GGATCCGGAT CCAGCAAAAG CAGGTAGATA TTGAAAGATG AGTCTTCTAA CCGAGGT        57

(2) INFORMATION FOR SEQ ID NO:4:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:4:

TCTAGATCTA GATTACTCCA GCTCTATGCT GACAAATG        38

(2) INFORMATION FOR SEQ ID NO:5:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:5:

CGGGATCCAA AAAATGCATT TTAGAAGAAC GATGAG        36

-continued ( 2 ) INFORMATION FOR SEQ ID NO:6:

( i ) SEQUENCE CHARACTERISTICS:
       ( A ) LENGTH: 30 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:6:

CCCGCTCGAG CGATGAGTGG GGATTTTGTC                                             30